(12) United States Patent
Chicoine et al.

(10) Patent No.: US 7,942,857 B2
(45) Date of Patent: May 17, 2011

(54) SANITARY ABSORBENT ARTICLE ASSEMBLY INCLUDING AN INTEGRATED DISPOSAL SHEET

(75) Inventors: Annie Chicoine, Montreal (CA); Christian Tremblay, Repentigny (CA)

(73) Assignee: Johnson & Johnson Inc. (CA)

( * ) Notice: Subject to any disclaimer, the term of this patent is extended or adjusted under 35 U.S.C. 154(b) by 645 days.

(21) Appl. No.: 11/957,864

(22) Filed: Dec. 17, 2007

(65) Prior Publication Data
US 2009/0105681 A1    Apr. 23, 2009

Related U.S. Application Data

(60) Provisional application No. 60/981,645, filed on Oct. 22, 2007.

(51) Int. Cl.
*A61F 13/15* (2006.01)
*A61B 17/06* (2006.01)

(52) U.S. Cl. ......... 604/385.02; 604/385.04; 604/385.13; 604/385.03; 206/440

(58) Field of Classification Search ............ 604/385.02, 604/385.04, 385.03, 385.01, 385.13; 206/440
See application file for complete search history.

(56) References Cited

U.S. PATENT DOCUMENTS
| | | | |
|---|---|---|---|
| 4,964,859 A | 10/1990 | Feldman | |
| 5,037,414 A | 8/1991 | Booth | |
| 6,063,065 A * | 5/2000 | Costa | 604/385.02 |

FOREIGN PATENT DOCUMENTS
| | | |
|---|---|---|
| FR | 2699401 A | 6/1994 |
| GB | 868299 A | 5/1961 |

OTHER PUBLICATIONS

European Search Report dated Jan. 22, 2009 for EP Appln. No. 08253404.1.

* cited by examiner

*Primary Examiner* — Jacqueline F Stephens (57) ABSTRACT

The present invention relates to sanitary absorbent articles and in particular to a sanitary absorbent article assembly including an integrated disposal sheet for disposal of a soiled absorbent article.

4 Claims, 7 Drawing Sheets

Fig. 14

SANITARY ABSORBENT ARTICLE ASSEMBLY INCLUDING AN INTEGRATED DISPOSAL SHEET

CROSS REFERENCE TO RELATED APPLICATIONS

This application claims priority to Application No. 60/981,645 filed on Oct. 22, 2007, the entire contents of which are incorporated by reference herein.

FIELD OF THE INVENTION

The present invention relates to sanitary absorbent articles and in particular to a sanitary absorbent article assembly including an integrated disposal sheet for disposal of a soiled absorbent article.

BACKGROUND OF THE INVENTION

Women often experience difficulty in deciding how to dispose of a soiled sanitary article such as a sanitary napkin. In general, there are two commonly used methods to dispose of a soiled sanitary article. One method involves the disposal of the soiled sanitary article in the toilet. The other commonly used method involves wrapping the used article, usually in toilet paper, and placing the wrapped article in the trash. Both methods can be problematic and may result in plumbing problems with the former method or the presence of odor in the trash with the latter method.

Various proposed solutions have been disclosed in the prior art for solving the above described problem. However, such proposed solutions are generally characterized by two shortcomings. Either the proposed solutions are complex in use requiring extensive manipulation of the either the soiled sanitary napkin or the disposal means (e.g. such as a disposal bag) or in the alternative the disposal means is not easily accessible by the user at the time of disposal.

In view of the foregoing the inventors of the present disclose herein a sanitary napkin assembly that includes an integrated disposal sheet that is easy to use and is easily accessible at the time of disposal.

SUMMARY OF THE INVENTION

In view of the foregoing the present invention provides, according to a first aspect of the invention, a sanitary article assembly including a sanitary article having a garment facing surface and an adhesive arranged on the garment facing surface for securing the sanitary article to an undergarment during use, the sanitary article having a trifolded configuration prior to use, the trifolded configuration defining a first end portion of the sanitary article, a second end portion of the sanitary article and an intermediate portion arranged between the first end portion and the second end portion, a disposal sheet having a folded configuration wherein the disposal sheet is attached to the garment facing surface and the disposal sheet extends over only a portion of the adhesive thereby permitting attachment of the sanitary article to an undergarment while the disposal sheet is simultaneously attached to the garment facing surface of said napkin, the disposal sheet further having a unfolded configuration, wherein the disposal sheet in the unfolded configuration includes a first wall and a second wall arranged in opposed relationship to the first wall, and the disposal sheet includes a first portion that corresponds in location to the first end portion of the sanitary article, a second portion that corresponds in location to the second end portion of the sanitary article, and a third portion that corresponds in location with the intermediate portion of the sanitary article, the second wall being arranged in the first portion and having a length that does not extend beyond the first portion, the first wall and second wall cooperating to define a pocket therebetween.

The present invention provides, according to a second aspect of the invention, a method of packaging, using and disposing of a sanitary article including the steps of providing a sanitary article having a trifolded configuration prior to use, the sanitary article having a garment facing surface and an adhesive arranged on the garment facing surface for securing the sanitary article to an undergarment during use, the trifolded configuration defining a first end portion of the sanitary article, a second end portion of the sanitary article and an intermediate portion arranged between the first end portion and the second end portion, providing a disposal sheet, the disposal sheet having folded configuration wherein the disposal sheet is attached to the garment facing surface and the disposal sheet extends over only a portion of the adhesive, packaging the trifolded sanitary article and the disposal sheet in an overwrap for protecting the sanitary and disposal sheet prior to use, removing the sanitary article from the overwrap, arranging the sanitary article on a surface of an undergarment in an unfolded configuration such that the garment facing surface is arranged in surface to surface contact with the undergarment and the disposal sheet is arranged in intermediate relationship between the sanitary article and the undergarment, removing the sanitary article from the undergarment when the sanitary article is in a soiled condition, unfolding the disposal sheet from the folded configuration to a unfolded configuration wherein the disposal sheet in the unfolded configuration includes a first wall and a second wall arranged in opposed relationship to a outer surface of the first wall, and the disposal sheet includes a first portion that corresponds in location to the first end portion of the sanitary article, a second portion that corresponds in location to the second end portion of the sanitary article, and a third portion that corresponds in location with the intermediate portion of the sanitary article, the second wall being arranged in the first portion and having a length that does not extend beyond the first portion, the second wall and the first wall cooperating to define a pocket, folding the first and second portions of the disposal sheet such that they are arranged in overlapping relationship relative to the third portion of the disposal sheet, the disposal sheet being folded while the correspond portions of the napkin are attached thereto such that the first and second end portions of the sanitary article are arranged in overlapping relationship relative to the intermediate portion of the sanitary article, inverting the pocket to receive the folded sanitary article within the pocket.

The present invention provides, according to a third aspect of the invention, a method of packaging a sanitary article including the steps of providing a sanitary article having a trifolded configuration prior to use, the sanitary article having a garment facing surface and an adhesive arranged on the garment facing surface for securing the sanitary article to an undergarment during use, the sanitary article having a trifolded configuration prior to use, the trifolded configuration defining a first end portion of the sanitary article, a second end portion of the sanitary article and an intermediate portion arranged between the first end portion and the second end portion, providing a disposal sheet, the disposal sheet having folded configuration wherein the disposal sheet is attached to the garment facing surface and the disposal sheet extends over only a portion of the adhesive, and packaging the trifolded sanitary article and the disposal sheet in an overwrap for protecting the sanitary and disposal sheet prior to use.

The present invention provides, according to a fourth aspect of the invention, a sanitary article assembly including a sanitary article having a garment facing surface and an adhesive arranged on the garment facing surface for securing the sanitary article to an undergarment during use, a disposal sheet having a folded configuration wherein the disposal sheet is attached to the garment facing surface and the disposal sheet extends over only a portion of the adhesive thereby permitting attachment of the sanitary article to an undergarment while the disposal sheet is simultaneously attached to the garment facing surface of said napkin, the disposal sheet further having a unfolded configuration, wherein the disposal sheet in the unfolded configuration includes a first wall and a second wall arranged in opposed relationship to the first wall, the first wall and second wall cooperating to define a pocket therebetween, the pocket being structured and arranged to receive the sanitary article after use.

BRIEF DESCRIPTION OF THE DRAWINGS

Examples of embodiments of the present invention will now be described with reference to the drawings, in which.

DETAILED DESCRIPTION OF THE INVENTION

Referring to FIGS. 1-4 the sanitary article assembly 10 according to the present invention generally includes an overwrap 12, a sanitary napkin 14 and a disposal sheet 16. Although the invention will be described herein with reference to a sanitary napkin 14 the invention may be utilized with other disposable sanitary absorbent articles such as adult incontinence products, panty liners, diapers and the like.

Figure 1:
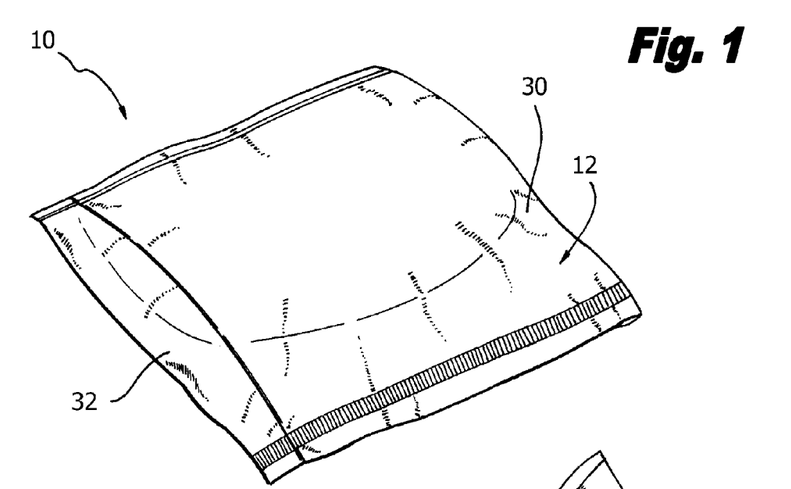
FIG. 1 is a perspective view of a sanitary article assembly according to the present invention showing the overwrap thereof in a closed configuration.
Figure 3:
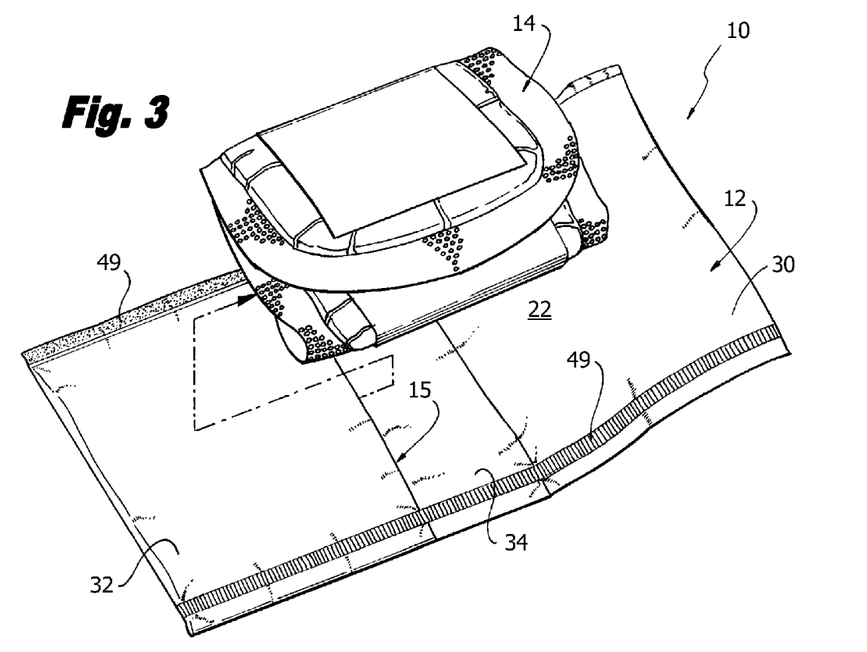
FIG. 3 is a perspective view of the sanitary article assembly depicting the removal of the sanitary article from the overwrap.

As best seen in FIG. 1 and FIG. 3 the sanitary napkin 14, prior to use, is arranged in a trifolded configuration and contained within the overwrap 12. The overwrap 12 is shown in a closed configuration in FIG. 1 with the sanitary napkin 14 contained within the overwrap 12. The overwrap 12 is also arranged in a trifolded configuration so as to define a pouch 15 for receiving the napkin 14 prior to use. The overwrap 12 is preferably constructed from a liquid impermeable polymeric film such as polyethylene or polypropylene, although other suitable liquid impermeable materials may also be employed.

The closed configuration of the overwrap shown in FIG. 1 is the configuration in which the user would find the overwrap 12 and sanitary napkin 14 prior to use. FIG. 3 shows the overwrap 12 in an open configuration enabling the user to manually remove the sanitary napkin 14 from the overwrap 12 for use. It is noted that overwrap 12 may be easily manually opened from the configuration shown in FIG. 1 to the configuration shown in FIG. 3.

Figure 2:
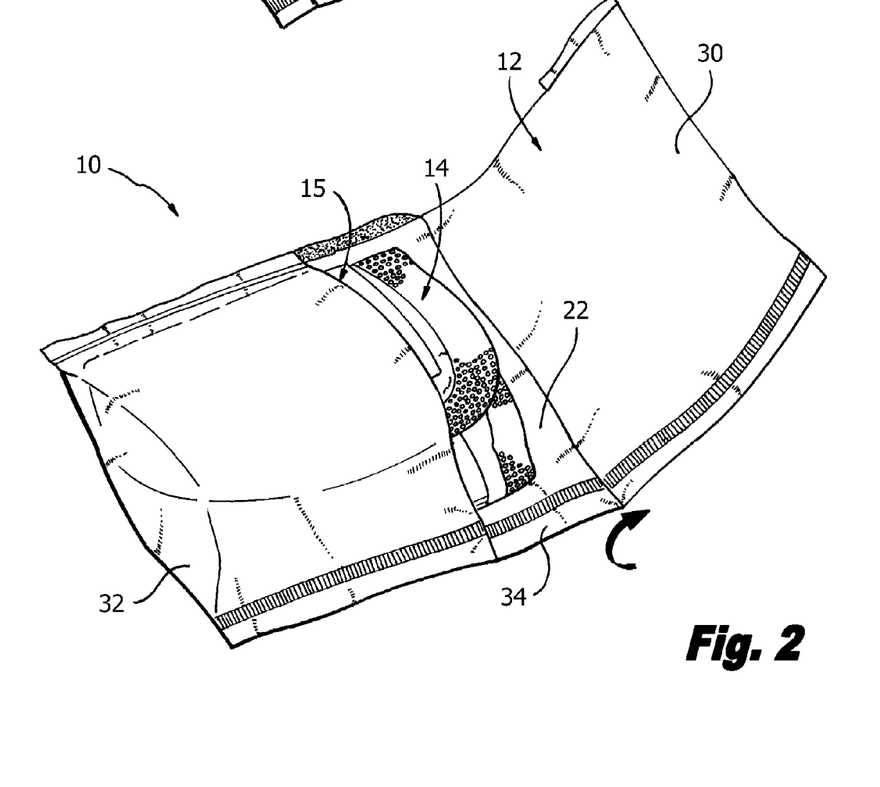
FIG. 2 is a perspective view of the sanitary article assembly shown in FIG. 1 showing the overwrap thereof in an opened configuration.

As shown in FIGS. 1-3, the overwrap 12 generally includes a first end portion or tri-section 30, a second end portion or tri-section 32 and an intermediate portion or tri-section 34. As best seen in FIG. 1, when the overwrap 12 is in the closed configuration prior to use the first end portion 30 is arranged in overlapping relationship with the second end portion 32. In the closed configuration, the first end portion 30, second end portion 32 and intermediate portion 34 are preferably secured to one another along their respective edges by means of a crimp seal 49. In this manner, the overwrap 12 is maintained in the closed configuration shown in FIG. 1 to maintain the sanitary napkin 14 in a hygienic state until the user is ready to use the sanitary napkin 14.

Once a user is ready to the use the napkin 14 the user may manually open the overwrap 12 from the closed configuration shown in FIG. 1 to the open configuration shown in FIG. 3 by unfolding the first end portion 30 of the overwrap from its overlapping condition with end portion 32 to thereby break the crimp seals 49 and place the overwrap 12 in the open configuration shown in FIG. 3. Once the overwrap 12 is placed in the open configuration shown in FIG. 3 the user may access the napkin 14 for use.

Figure 4:
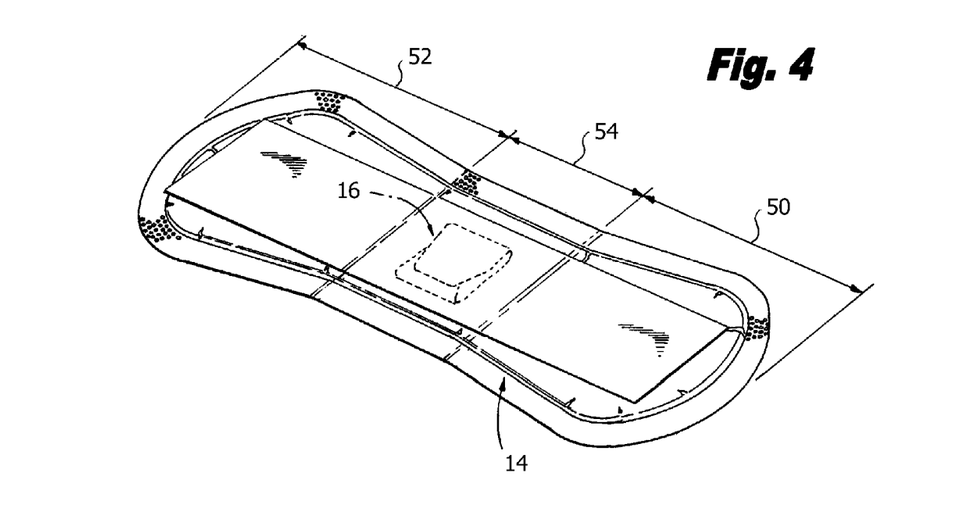
FIG. 4 is a bottom perspective view of the sanitary article of the sanitary article assembly according to the present invention.

As discussed above, the sanitary napkin 14 is arranged in a trifolded configuration in the overwrap 12 prior to use. Due to the trifolded configuration of the sanitary napkin 14 prior to use, the sanitary napkin 14 is generally divided into three portions. In particular as shown in FIG. 4, the napkin includes a first end portion 50, a second end portion 52 and an intermediate portion 54 defined between the first 50 and second 52 end portions. These "portions" are defined by the fold lines resultant from the trifolded configuration of the napkin prior to use.

Figure 5:
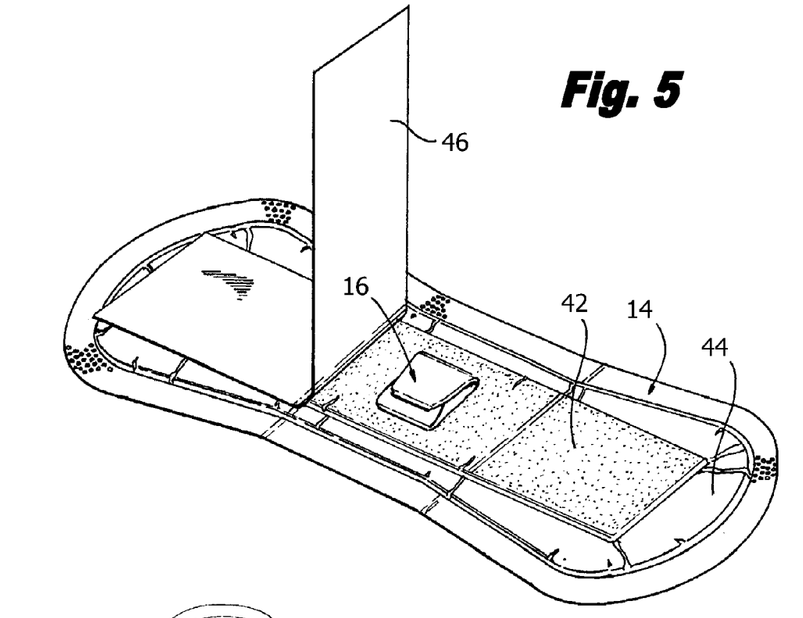
FIG. 5 is a bottom perspective view of the sanitary article shown in FIG. 4 with a release member thereof partially removed from the sanitary article.
Figure 6:
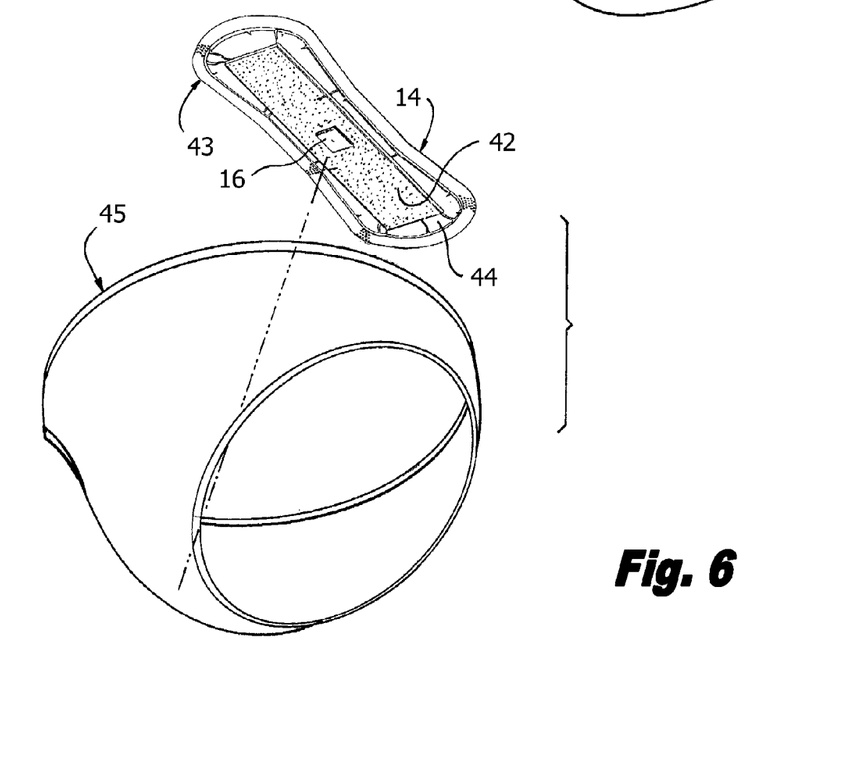
FIG. 6 is a schematic view showing the manner of attachment of the sanitary article to an undergarment.

As shown in FIG. 6 the sanitary napkin 14 includes a body facing surface 43 and a garment facing surface 44. In one preferred embodiment of the invention shown in FIGS. 4 and 5, the sanitary napkin 14 is provided with a garment attachment adhesive 42 arranged on the garment facing surface 44 of the napkin 14 which functions to securely attach the sanitary napkin 14 to an undergarment 45 during use. The adhesive 42 is preferably covered by a removable release member 46 to protect the garment attachment adhesive 42 prior to use of the napkin 14. In another embodiment of the invention, not shown in the Figures, the removable release member 46 may be omitted. However, in such an embodiment, the inner surface 22 of the overwrap 12 should be provided with a nonstick surface coating, e.g. silicone, to facilitate the removal of the napkin 14 from the overwrap 12.

During use of the napkin 14, as shown in FIG. 6, the disposal sheet 16 is arranged in a folded configuration and is attached to the garment facing surface 44 of the napkin. In particular, the disposal sheet 16 is secured to garment attachment adhesive 42 during use of the napkin 14. In order to insure that the disposal sheet 14 does not interfere with the attachment of the napkin 14 to the undergarment 45 it is preferred that the disposal sheet 16, in its folded configuration, extends over only a relatively small portion of the garment attachment adhesive 42. In particular, it is preferred that the disposal sheet 14, in its folded configuration, extend over only about 1% to about 20% of the coverage area of the garment attachment adhesive 42. In the particular embodiment of the invention shown in the Figures, the disposal sheet 14 in its folded configuration is arranged in the intermediate portion 54 of the napkin 14 and does not extend into either of the other portions of the napkin, i.e. portions 50 and 52. It is possible that the disposal sheet 14, in its folded configuration, be arranged in other portions of the napkin, i.e. portions 50 or 52, however it is preferable that the disposal sheet 14 be limited in position to a single portion, i.e. it is preferable that the disposal sheet 14 not extend into more than one portion of the napkin 14 when it is in its folded configuration.

Figure 7:
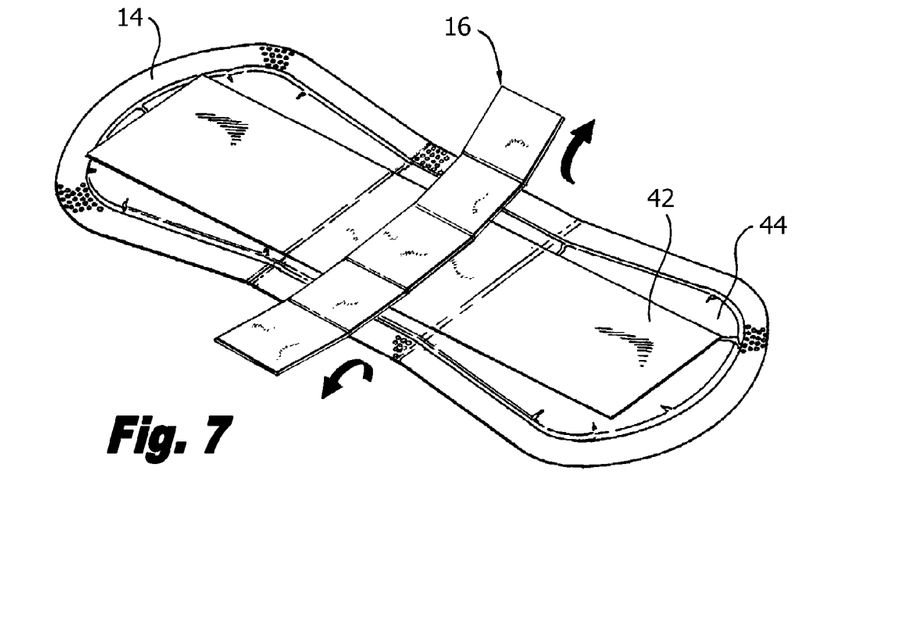
FIG. 7 is a schematic view showing the manner of deploying the disposal sheet of the sanitary article assembly according to the present invention.
Figure 8:
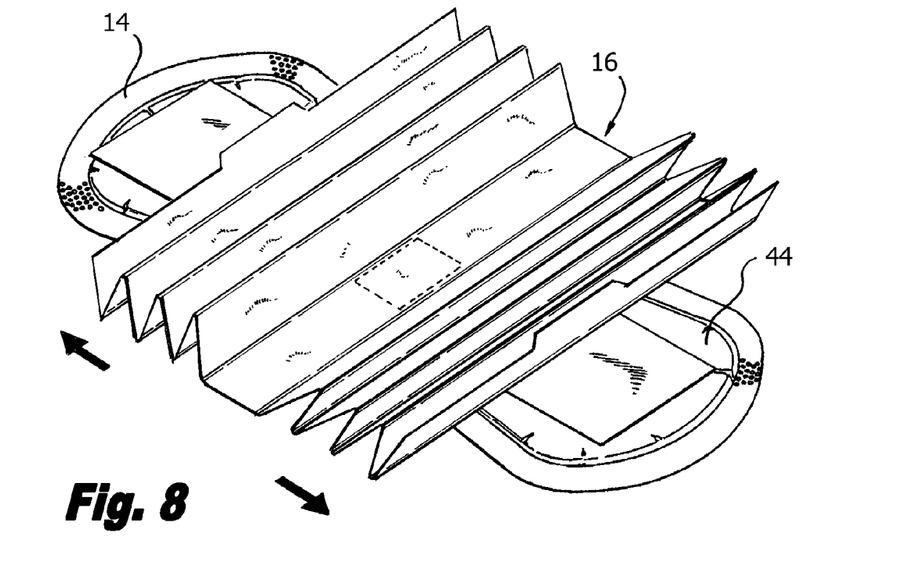
FIG. 8 is a schematic view showing the further deployment of the disposal sheet shown in FIG. 7.
Figure 9:
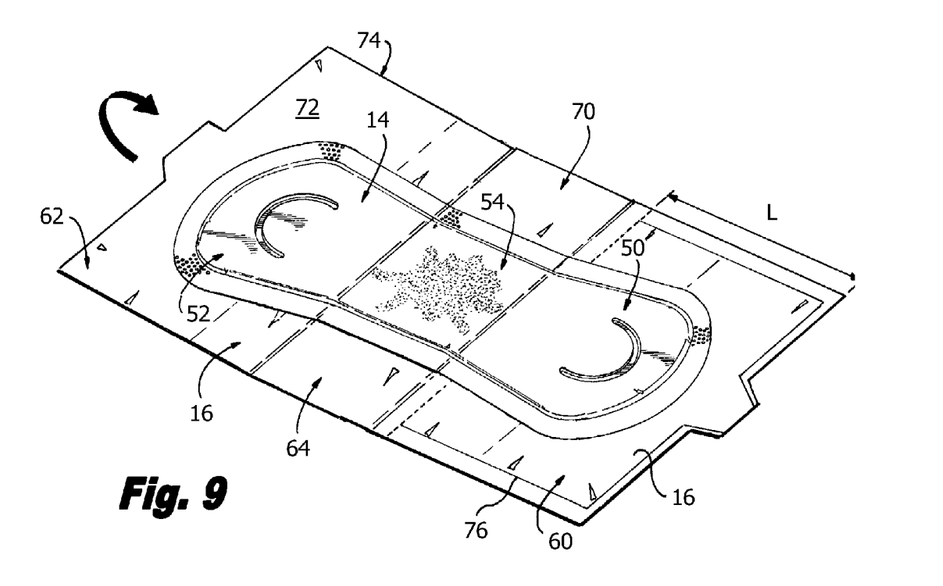
FIG. 9 is a perspective view of the disposal sheet shown in FIG. 7 in a fully deployed configuration.

After the napkin 14 has been attached to the undergarment 45 and used as desired, the soiled napkin 14 may be removed from the undergarment 45. As shown in FIGS. 7-9, after the soiled napkin 14 is removed from the undergarment 45, the disposal sheet 16 may be unfolded from its folded configuration shown in FIG. 6 to an unfolded configuration shown in FIG. 9. In the unfolded configuration shown in FIG. 9, the disposal sheet 16 generally includes a first portion 60, a second portion 62 and a third portion 64 arranged between the first 60 and second 62 portions. When the disposal sheet 16 is in the unfolded configuration the first portion 60 thereof corresponds in location to the first end portion 50 of the napkin 14, the second portion 62 thereof corresponds in location to the second end portion 52 of the napkin 14, and the third portion 64 thereof corresponds in location to the intermediate portion 54 of the napkin 14.

Figure 11:
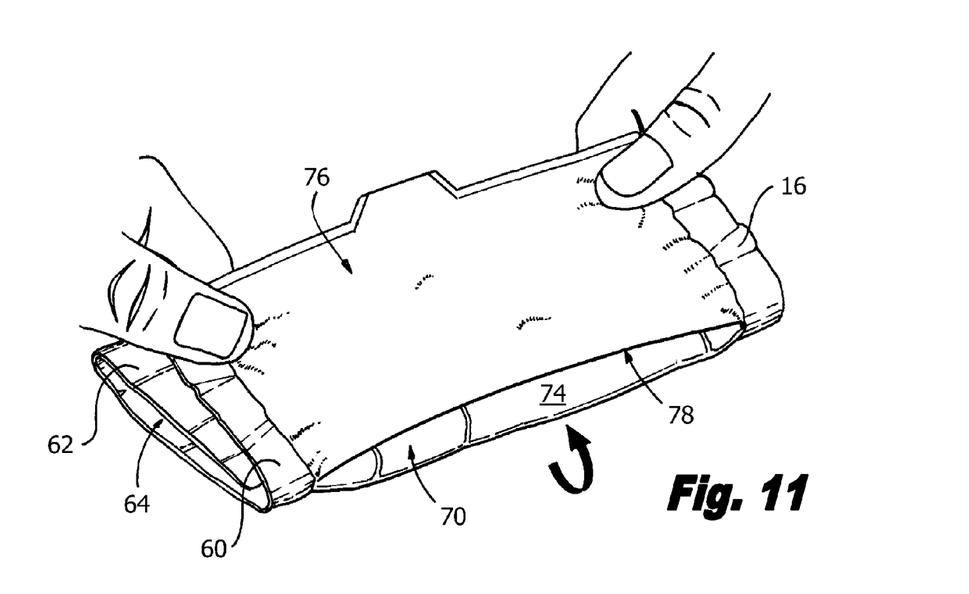
Figure 12:
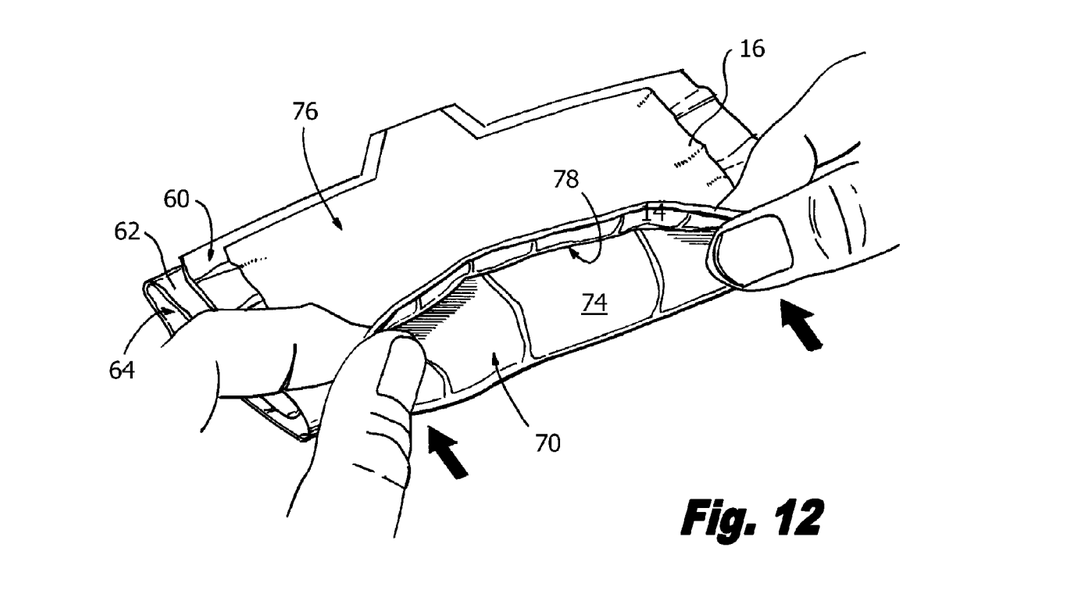
Figure 13:
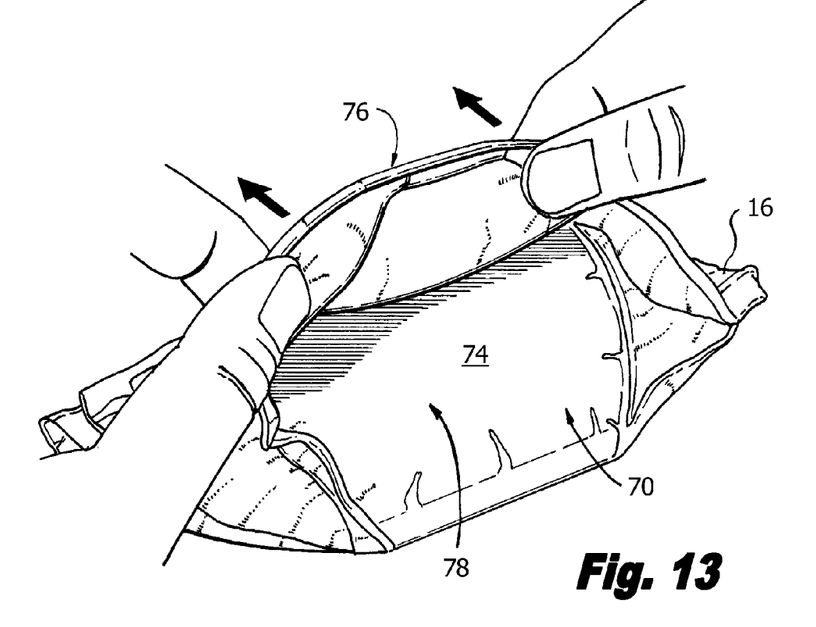
Figure 14:
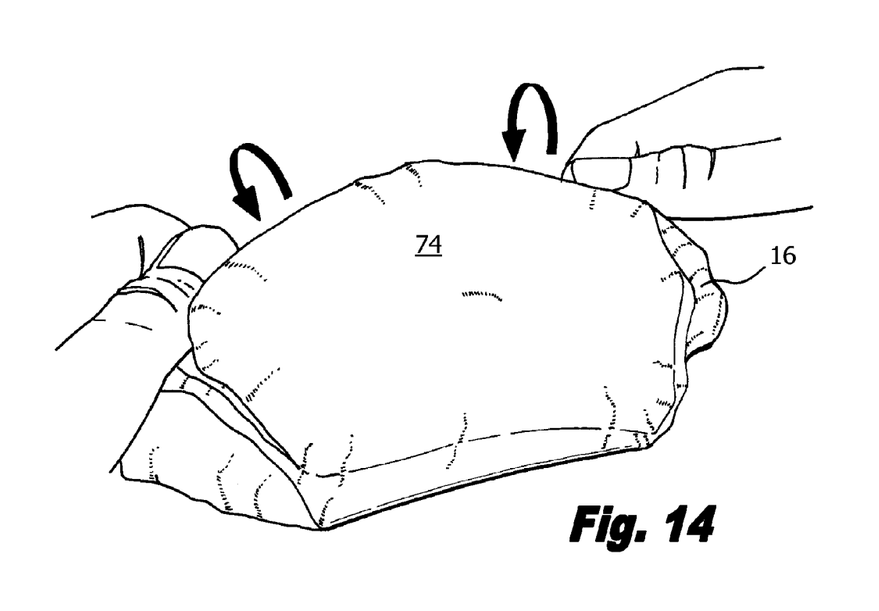

In the unfolded configuration the disposal sheet 16 includes a first wall 70 having an inner surface 72 and an outer surface 74. When in the unfolded configuration the inner surface 72 of the first wall 70 is arranged in surface to surface contact with the garment facing surface 44 of the sanitary napkin 14. As best seen in FIG. 11, the disposal sheet further includes a second wall 76 that is arranged in opposed relationship to the outer surface 74 of the first wall 70. The second wall 76 is preferably dimensioned such that it is located only with the first portion 60 of the disposal sheet 16 when the disposal sheet 16 is in its unfolded configuration. In other words, as shown in FIG. 9, the second wall 76 has a length "L" that does not extend beyond the first portion 60. As best seen in FIG. 11, the second wall 76 is secured to the first wall 70 along three of its edges and open along one of its edges to thereby define a pocket 78 between the first wall 70 and second wall 76.

Figure 10:
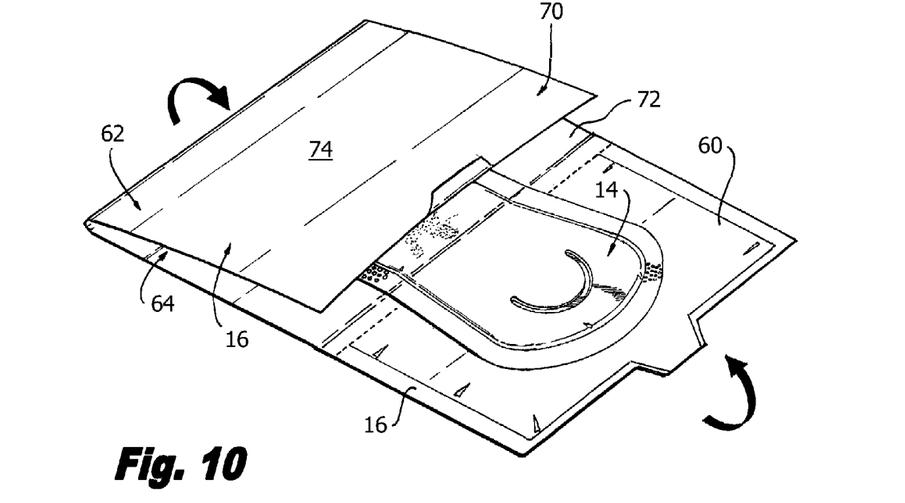
FIGS. 10, 11, 12, 13 and 14 are schematic views that depict the steps of wrapping a soiled sanitary article in the disposal sheet prior to disposal of the soiled sanitary article.

A method of using the absorbent article assembly 10 according to the present invention will now be described with reference to FIGS. 1-14. As shown in FIGS. 1-3 the napkin 14 is provided in a trifolded configuration prior to use and packaged within the overwrap 12. When a user desires to access the napkin 14 the user manually opens the overwrap 12 from the first closed configuration shown in FIG. 1 to a second open configuration shown in FIG. 3. The user may then remove the napkin 14 from the overwrap 12 for use. After the user has removed the napkin 14 from the overwrap 12, the user may then remove the release member 46 from the napkin 14 to thereby expose the garment attachment adhesive 42. After removing the release member 46 the user may then secure the napkin to an undergarment 45 as shown in FIG. 6. When the user has worn the napkin 14 for the desired period of time the user may remove the napkin 14 from the undergarment and unfold the disposal sheet 16 from its folded configuration shown in FIG. 6 to the unfolded configuration shown in FIG. 8. Once the disposal sheet is arranged in the unfolded configuration shown in FIG. 9, the user may then fold the second portion 62 of the disposal sheet 16 such that it is arranged in overlapping relationship to the third intermediate portion 64 of the disposal sheet 16, as shown in FIG. 10. Then, the user may fold the first portion 60 of the disposal sheet such that it is arranged in overlapping relationship to the second 62 and third 64 portions of the disposal sheet. After the first 60, 62 and third 64 portions are arranged in overlapping relationship as shown in FIG. 11, the user may then invert the pocket 78 defined between the first wall 70 and second wall 76. In other words, the user turns the pocket 78 inside out as shown in FIGS. 11-14. By turning the pocket 78 inside out as described the pocket 78 is closed and the soiled napkin 14 is securely maintained within the closed enclosure. The user may then conveniently dispose of the sanitary napkin as desired.

It has been recognized by the present inventors that a soiled sanitary napkin often has a volume that is sufficiently greater than the volume of the same napkin in the dry state. Accordingly, it is preferable that the second wall 76 of the disposal sheet 16 be dimensioned such that the pocket 78 defined between the first wall 70 and second wall 76 has a volume sufficient to receive a sanitary napkin having a volume of about 1.5 times to about 5 times a volume of the sanitary napkin 14 in a dry condition.

In view of the above the inventors of the present invention have provided a sanitary article assembly that overcomes the shortcomings of the prior art. In particular the inventors have provided a sanitary article assembly that includes an integrated disposal sheet that is easy to use and is also easily accessible at the time of disposal of the sanitary article.

The invention claimed is:

1. A method of packaging, using and disposing of a sanitary article comprising the steps of:
provinding a sanitary article having a trifolded configuration prior to use, the sanitary article having a garment facing surface and an adhesive arranged on the garment facing surface for securing the sanitary article to an undergarment during use, the trifolded configuration defining a first end portion of the sanitary article, a second end portion of the sanitary article and an intermediate portion arranged between the first end portion and the second end portion;
providing a disposal sheet, the disposal sheet having folded configuration wherein the disposal sheet is attached to the garment facing surface and the disposal sheet extends over only a portion of the adhesive;
packaging the trifolded sanitary article and the disposal sheet in an overwrap for protecting the sanitary and disposal sheet prior to use;
removing the sanitary article from the overwrap;
arranging the sanitary article on a surface of an undergarment in an unfolded configuration such that the garment facing surface is arranged in surface to surface contact with the undergarment and the disposal sheet is arranged in intermediate relationship between the sanitary article and the undergarment;
removing the sanitary article from the undergarment when the sanitary article is in a soiled condition;
unfolding the disposal sheet from the folded configuration to a unfolded configuration wherein the disposal sheet in the unfolded configuration includes a first wall and a second wall arranged in opposed relationship to a outer surface of the first wall, and the disposal sheet includes a first portion that corresponds in location to the first end portion of the sanitary article, a second portion that corresponds in location to the second end portion of the sanitary article, and a third portion that corresponds in location with the intermediate portion of the sanitary article, the second wall being arranged in the first portion and having a length that does not extend beyond the first portion, the second wall and the first wall cooperating to define a pocket;

folding the first and second portions of the disposal sheet such that they are arranged in overlapping relationship relative to the third portion of the disposal sheet, the disposal sheet being folded while the correspond portions of the napkin are attached thereto such that the first and second end portions of the sanitary article are arranged in overlapping relationship relative to the intermediate portion of the sanitary article;

inverting the pocket to receive the folded sanitary article within the pocket.

2. The method according to claim 1, wherein the disposal sheet in the folded configuration covers from about 1% to about 20% of the adhesive.

3. The method according to claim 1, wherein the pocket has a sufficient volume to entirely receive the sanitary article within the pocket.

4. The method according to claim 1, wherein the pocket has a sufficient volume to receive a sanitary article having a volume of about 1.5 times to about 5 times a volume of the sanitary article in a dry condition.

* * * * *